United States Patent [19]

Forester

[11] Patent Number: 4,889,614

[45] Date of Patent: Dec. 26, 1989

[54] METHODS FOR RETARDING COKE FORMATION DURING PYROLYTIC HYDROCARBON PROCESSING

[75] Inventor: David R. Forester, Conroe, Tex.

[73] Assignee: Betz Laboratories, Inc., Trevose, Pa.

[21] Appl. No.: 349,014

[22] Filed: May 9, 1989

[51] Int. Cl.$^4$ .............................................. C07C 3/30
[52] U.S. Cl. .............................. 208/48 AA; 585/659;
585/950; 585/649; 585/650; 208/48 R
[58] Field of Search ................ 208/48 AA; 585/659,
585/950, 649, 650

[56]  References Cited

U.S. PATENT DOCUMENTS

| | | | |
|---|---|---|---|
| 2,285,752 | 6/1942 | Van Ess | 252/52 |
| 2,415,353 | 2/1947 | Johnston et al. | 252/33.2 |
| 2,468,831 | 5/1949 | Miller | 260/683.5 |
| 3,105,810 | 10/1963 | Miller et al. | 208/48 |
| 3,322,664 | 5/1967 | Paterson et al. | 208/48 |
| 3,328,284 | 6/1967 | Godar | 208/48 |
| 3,381,051 | 4/1968 | Bergier et al. | 260/679 |
| 3,480,689 | 11/1969 | Bohrer | 260/683 |
| 3,531,538 | 9/1970 | Duerksen et al. | 260/674 |
| 3,617,478 | 11/1971 | King et al. | 208/48 |
| 3,617,479 | 11/1971 | King et al. | 208/48 |
| 3,920,572 | 11/1975 | King et al. | 252/75 |
| 3,958,624 | 6/1976 | Peeler et al. | 165/1 |
| 4,222,853 | 9/1980 | Scherrer et al. | 208/48 |
| 4,233,138 | 11/1980 | Rollmann et al. | 208/48 AA |
| 4,264,363 | 4/1981 | Cech | 106/14.28 |
| 4,297,150 | 10/1981 | Foster et al. | 148/6.3 |
| 4,454,021 | 6/1984 | Watanabe et al. | 208/48 |
| 4,680,421 | 7/1987 | Forester et al. | 585/648 |
| 4,692,313 | 9/1987 | Walanabe et al. | 208/48 AA |
| 4,747,931 | 5/1988 | Forester et al. | 208/48 AA |
| 4,756,820 | 7/1988 | Reid et al. | 208/48 |

FOREIGN PATENT DOCUMENTS 0133570  1/1979  Fed. Rep. of Germany ........ 208/48 AA Primary Examiner—Helane Myers
Attorney, Agent, or Firm—Bruce E. Peacock; Alexander D. Ricci

[57]  ABSTRACT

Methods for inhibiting coke formation in pyrolytic reactors and furnaces are disclosed wherein effective alkaline earth metal salt coke retardant treatments are used. Exemplary coke retardant treatments include magnesium and calcium salts such as the acetate, chloride, and nitrate, and magnesium sulfate salt.

16 Claims, No Drawings

METHODS FOR RETARDING COKE FORMATION DURING PYROLYTIC HYDROCARBON PROCESSING

FIELD OF THE INVENTION

The present invention pertains to methods for inhibiting the formation and deposition of coke deposits during the high temperature processing or cracking of hydrocarbons by the use of certain magnesium and calcium salts dissolved in a liquid solvent.

BACKGROUND OF THE INVENTION

Coke deposition is generally experienced when hydrocarbon liquids and vapors contact the hot metal surfaces of processing equipment. While perhaps not entirely technically understood, because of the complex makeup of the hydrocarbons, the hydrocarbons at elevated temperatures and in contact with hot metallic surfaces undergo various changes through either chemical reactions and/or decomposition of various unstable components of the hydrocarbon. The undesired products in many instances include coke, polymerized products, deposited impurities and the like. Whatever the undesired product that may be formed, the result is the same, i.e., reduced economies of the process. If these deposits are allowed to remain unchecked, heat transfer, throughput and overall productivity are detrimentally effected. Moreover, downtime is likely to be encountered due to the necessity of either replacing and/or cleaning of the affected parts of the processing system.

While the formation and type of undesired products are dependent upon the hydrocarbon being processed and the conditions of the processing, it may generally be stated that such products can be produced at temperatures as low as 100° F.; but are much more prone to formation as the temperature of the processing system and the metal surfaces thereof in contact with the hydrocarbon increase. At these temperatures, coke formation is likely to be produced regardless of the type hydrocarbon being charged. The type coke formed, i.e., amorphous, filamentous or pyrolytic, may vary somewhat; however, the probability of the formation of such is quite high.

As indicated in U.S. Pat. Nos. 3,531,394 and 4,105,540 the teachings of which are incorporated herein by reference, coke formation and deposition are common problems in ethylene (olefin) plants which operate at temperatures where the metal surfaces in contact with the hydrocarbon are sometimes at 1600° F. and above. The problem is prevalent in the cracking furnace coils as well as in the transfer line exchangers where pyrolytic type coke formation and deposition is commonly encountered. Ethylene plants, often referred to generally was "olefin plants", originally produced simple olefins such as ethylene, propylene, butenes and butadiene from a feed of ethane, propane, butanes and mixtures thereof. Later developments in the area of technology however, have led to the cracking of heavier feedstocks, because of their availability, to produce aromatics and pyrolysis gasoline as well as light olefins. Feedstocks now include light naphtha, heavy naphtha and gas oil. According to the thermal cracking processes utilized in olefin plants, the feedstocks are cracked generally in the presence of steam in tubular pyrolysis furnaces. The feedstock is preheated, diluted with steam and the mixture heated in the pyrolysis furnace to about 1500° F. and above, most often in the range of 1500° F. to 1650° F. The effluent from the furnace is rapidly quenched by direct means or in exchangers which are used to generate high pressure steam at 400 to 800 psig for process use. This rapid quench reduces the loss of olefins by minimizing secondary reactions. The cooled gas then passes to the prefractionator where it is cooled by circulating oil streams to remove the fuel oil fraction. In some designs, the gas leaving the quench exchanger is further cooled with oil before entering the prefractionator. In either case, the heat picked up by the circulating oil stream is used to generate steam and to heat other process streams. The mixture of gas and steam leaving the prefractionator is further cooled in order to condense the steam and most of the gasoline product in order to provide reflux for the prefractionator. Either a direct water quench or heat exchangers are used for this cooling duty.

After cooling, cracked gas at, or close to atmospheric pressure, is compressed in a multistage compression system to much higher pressures. There are usually four or five stages of compression with interstage cooling and condensate separation between stages. Most plants have hydrocarbon condensate stripping facilities. Condensate from the interstage knockout drums is fed to a stripper where the $C_2$ hydrocarbons and lighter, are separated. The heavier hydrocarbons are fed to the depropanizer.

PRIOR ART

A variety of approaches have been proposed to eliminate coke formation during the elevated temperature processing of hydrocarbonaceous mediums. For example, U.S. Pat. No. 4,680,421 (Forester et al.—of common assignment herewith) teaches utilization of ammonium borates, specifically ammonium biborate and ammonium pentaborate that are preferably dissolved in a glycollic solvent. Of similar import is U.S. Pat. No. 4,756,820 (Forester et al.—also of common assignment herewith) which discloses that boron oxides, borates, borate esters, peroxyborates, boranes, organoboranes, borazine and salts of boron may be used.

Alkaline earth salts of alkyl benzene sulfonic acid or oil soluble petroleum sulfonic acid are taught in U.S. Pat. No. 3,105,810 (Miller et al.) as being useful in preventing fouling of metal conductors that are in contact with napthas, gas oils and crude oils when the same are heat treated at temperatures of 200°–1100° F. U.S. Pat. No. 3,328,284 (Godar) teaches two component mixtures that are useful in coke retardancy applications at temperatures on the order of 200°–800° F. The mixtures incorporate both oxyalkylated phenolic compounds and organic sulfonate salts including the Group IIA organic sulfonate salts (Col. 3, line 63).

A molten metal coating is provided in a pyrolysis or thermal cracking furnace in U.S. Pat. No. 3,480,689 (Bohrer) in order to mitigate against carbon deposition. The molten metal may comprise magnesium.

Although not directed toward pyrolytic operations, Cech, in U.S. Pat. No. 4,264,363, teaches that complex mixtures comprising a non-Newtonian colloid that includes certain alkaline earth metal salts of oil soluble carboxylic and sulfonic acids can be used in a coating composition to protect metal against corrosion. The metal sats may be metal salts of inorganic acids and low molecular weight organic acids such as formic, acetic and propionic acids (Col. 2, lines 28–40). Yet another coating composition comprising oxides of Ca, Mg, etc., is taught in U.S. Pat. No. 4,297,150 (Foster). U.S. Pat. No. 4,454,021 (Watanabe et al.) teaches incorporation of alkali metals, alkaline earth metals, alkali metal oxides, or alkaline earth metal oxides in solid solution or as a dispersed phase into the metal alloy or as a coating on the alloy in order to suppress carbon deposition.

Other patents that may be of interest include: U.S. Pat. Nos. 3,958,624 (Peeler et al.); 4,222,853 (Scherrer et al.); 3,617,478 (King et al.); 3,617,479 (King, Jr.); 3,322,664 (Paterson et al.); 2,468,831 (Miller); 2,415,353 (Johnston et al.); 2,285,752 (Van Ess); 3,920,572 (King et al.); 3,531,538 (Duerksen); and 3,381,051 (Bergier et al.).

Also, in many ethylene/propylene plants, sulfides have been used to deactivate furnace tube walls and to reduce coking. However, these materials are hazardous and limited in their coke retardant efficacy.

Despite the prior art efforts there remains a need for an inexpensive, but effective treatment for use to minimize the formation and deposition of coke particles on heated surfaces in a pyrolysis furnace cracking petroleum gases or liquids to make olefins such as in the cracking of propane to make ethylene/propylene.

There is an even more specific need to provide an effective treatment that is soluble in water or other inexpensive polar solvents so that the treatment may be dispersed in the hydrocarbon charge itself or added to the steam used to provide sufficient heat to effect cracking.

DESCRIPTION OF THE INVENTION

Generally, the invention entails utilizing certain alkaline earth metal salts such as calcium and magnesium salts to inhibit coke formation in pyrolytic processing applications.

The alkaline earth metal salts of the invention include the chlorides, nitrates and lower ($C_1$–$C_4$) alkanoic acid salts of both calcium and magnesium. Also included is magnesium sulfate. Laboratory data collected to date have shown the following to provide at least some effectiveness in reducing coke formation under simulated pyrolytic conditions:

magnesium acetate
magnesium nitrate
magnesium chloride
magnesium sulfate
calcium acetate
calcium nitrate
calcium chloride The methods are adapted to inhibit the formation and deposition of coke on metallic surfaces in contact with a hydrocarbon (either in liquid or gaseous form) which surfaces reach temperatures of 1400° F. and above (most often 1500°–2050° F.). These temperatures are commonly encountered in olefin plants as earlier indicated. In these systems, the components of the furnace (pyrolytic) as well as the ancillary parts are composed of ferrous metal. Iron, as well as iron alloys such as low and high carbon steel, and nickel-chromium-iron alloys are customarily used for the production of hydrocarbon processing equipment such as furnaces, transmission lines, reactors, heat exchangers, separation columns, fractionators, and the like.

It has been found that coking during the high temperature cracking of hydrocarbons may be significantly reduced on heated stainless steel surfaces utilized in conjunction with the test system described infra by use of the calcium and magnesium salts noted above. Accordingly, it is to be expected that coking will also be reduced on iron, chromium and nickel based metallurgical surfaces in contact with pyrolysis products in high temperature pyrolytic furnaces.

The calcium and magnesium salt treatment agents may be added directly to the hydrocarbon feedstock or charge before and/or during cracking, or the treatment may be mixed with steam carried to the cracking zone in accordance with conventional cracking techniques.

Preferably, the calcium and magnesium salts of the invention are dissolved in water, although other polar solvents such as alcohols (methanol, ethanol, etc.) and glycols may be used. At present, magnesium nitrate is the preferred treatment compound.

The calcium and magnesium compounds may be dissolved in the polar solvent in any concentration so as to produce a product to provide the necessary amount of the compound to any coke-prone environment to inhibit or reduce coking. Coking is a significant problem and if left untreated will eventually shut the operation down. Accordingly, it is desirable to ensure that the calcium or magnesium compound content of the solution and/or the product feed rate is high enough to ensure that an ample quantity of the calcium or magnesium compound mixes with or is dispersed in the hydrocarbonaceous medium during the pyrolytic cracking process. Accordingly, product formulation lends itself to great flexibility.

Generally, the product can contain, on a weight basis, from about 1–75% actives (calcium or magnesium salt compound) either dissolved or adequately dispersed in a carrier liquid, preferably polar solvent. To assure maintenance of the solution or dispersion during storage and transport, stabilizing agents and/or preservatives may also be added to the formulation.

Exemplary formulations include

| Exemplary formulations include | | |
|---|---|---|
|  | Preferred | Range |
| Active Ingredient | 5–50% | 1–75% |
| Carrier Liquid | 95–50% | 99–25% |

EXAMPLES

In order to establish the efficacy of the inventive concept, various tests were conducted utilizing a propane feedstock with dilution steam added to enhance cracking. The apparatus and procedure used for the testing were as follows:

APPARATUS

The High Temperature Fouling Apparatus (HTFA) consists of five subsections which together simulate the pyrolysis of gaseous hydrocarbons to make the light olefinic end products and the undesirable by-product, coke, that is formed on the heated metal surfaces during the pyrolysis reaction.

The feed preheat section is built of 316 stainless steel tubing and fittings and allows the mixing of nitrogen or oxygen containing gas with steam during the start up and shut down of the HTFA and the propane with steam during the actual test. Steam is supplied at 40 psig by a steam generator and nitrogen, oxygen containing gas, or propane are fed from compressed gas cylinders. The gases and steam are heated to about 300° F. at which point small amounts of water (blank test) or antifoulant is slowly injected into the stream by a syringe pump. The gases/antifoulant are further preheated to about 500° F. before flowing through a 13-foot long coiled 316 SS tube inside an electrically heated furnace. The gases are heated at a furnace temperature of approximately 1880° F. and exit the furnace at 1150°–1450° F.

Following the furnace tube, the gases travel through the coker rod assembly. This consists of a 316 SS rod which is electrically heated to 1500° F. while the gases flow around the heated rod inside a 316 SS shell. The rod is electrically heated through a silicon controlled rectifier (SCR), then through two 4 to 1 stepdown transformers in series to achieve low voltage (3-4 volts), high amperage (~200 amps) heating of the rod. A temperature controller is used to achieve power control through the SCR to obtain a 1500° F. rod temperature.

Upon exiting the coker rod, the gases pass through a condenser coil and then through three knock-out flasks in ice baths to remove the water (steam) from the product gases. The small amount of remaining entrained water vapor in the gases is removed by passing through drierite granules.

The specific gravity of the product gas is determined in a gas densitometer and the gases are analyzed using gas chromatography to determine yields. The remaining gases are vented through a safety hood exhaust.

TEST PROCEDURE The furnace was turned on and the temperature thereof was stabilized at 1300° F. while feeding nitrogen and steam. The coker rod was heated to 1500° F. The nitrogen was replaced with oxygen containing gas (air) and furnace temperatures were then slowly increased to 1500° F. over a period of ten minutes. Then the air was replaced with nitrogen and the coke inhibitor or water (blank), as the case may be, was injected into the mixed gas or steam line at about 300° F. gas temperature while the furnace temperature was slowly raised to 1880° F. over 20°–25 minutes.

Then the nitrogen feed was gradually switched to propane feed over about 5 minutes. The temperature of the furnace dropped due to the propane cracking reaction and was allowed to increase to the maximum attainable furnace temperature 1880° F. or less) over approximately a 30-minute period. The product gases were analyzed by gas chromatography and the temperatures, flowrates, pressures and product gas gravity recorded every 35 minutes during the 160-minute test on propane/steam feed. Gases exit the furnace tube at about 1150° F.–1450° F. and exit the coker shell at about 975°–1000° F. temperatures.

During a normal 160 minute run, approximately 3200–3300 grams of propane were fed and 1000–2000 grams of steam fed (determined from the condensate collected) for hydrocarbon to steam rates of about 1.6:1 to 3.2:1.

Following shutdown and cooling, the furnace tube and coker shell were cleaned and the coke collected and weighed. The coke was burned to determine how much was non-coke (metal corrosion products). These corrosion products (gray matter) were analyzed to be 69 wt. % $Fe_3O_4$, 13 wt. % NiO, 15 wt. % $Cr_2O_3$, 1 wt. % $SiO_2$, 1 wt. % $MnO_2$ and 1 wt. % loss on ignition. The composition is similar to 316 SS (68.4% Fe, 18% Cr, 11% Ni, 2.5% Mo and 0.1% carbon). After a series of blank (water) and antifoulant tests were conducted, a steam to coke relationship was determined for the blanks and the predicted coke values compared to observed coke values of the treatments to determine percent coke reduction.

RESULTS

Due to deterioration of the 316 SS furnace tube caused by repetitive heating to 1880° F. and cooling to 75° F., the tube required periodic replacement, usually every 20–30 runs. Hence, experiments were numbered by furnace tube and consecutive run no. During furnace tubes 18 to 22, a total of 22 control experiments were conducted. The observed coke values from these control experiments were found to fit a predicted coke equation of 5.32/condensate rate where the condensate rate is the volume of condensate collected at the end of the test in milliliters divided by the total time on steam in minutes. During furnace tubes 18, 19, or 21, seven different experiments were treated with water solutions of calcium or magnesium acetate. As shown in Table I, predicted coke values were determined for these experiments using the 5.32/condensate rate equation. Also, % coke reduction for each treated experiment was determined using the following equation:

$$\% \text{ coke reduction} = \left[1 - \frac{\text{Observed Coke}}{\text{Predicted Coke}}\right] \times 100\%$$

During furnace tubes 24 to 30, nineteen control runs were conducted and the observed coke values from these runs were determined to fit a predicted coke equation of 4.65/condensate rate. During furnace tubes 24 and 25, four propane/steam experiments were treated with water solutions of calcium or magnesium acetate as detailed in Table I. Using the condensate rate and the predicted coke and coke reduction equations, predicted coke values and % coke reductions were calculated for these experiments.

Finally, during furnace tubes 34 to 41, twenty-one control runs were conducted. The observed coke values were determined to fit the 7.38/condensate rate predicted coke equation. During this series of furnace tubes, a total of 22 HTFA experiments were treated with water solutions of calcium or magnesium salts as detailed in Table I. Similar to previous treated runs, predicted coke values and % coke reductions for these experiments were calculated as also shown in Table 1.

TABLE I

High Temperature Fouling Apparatus Results
1300–1500° F. Furnace Steam/Air Decoke;
1500–1880° F. Furnace Af/N2/Steam
1880° F. Furnace Propane (0.5 SCFM)/Steam/Af for 2.67 Hr.

| Run # | Steam Ml/Min | Antifoulant (ppm, Metal) | Coke Gms | Gray Gms | Pred (1) Coke Gms | % Coke (2) Reduction |
|---|---|---|---|---|---|---|
| 18-19 | 7.74 | 10% Ca(Ac)2/H2O(29,Ca)a | 0.44 | 0.05 | 0.69 | 36 |
| 19-5 | 5.35 | 10% Ca(Ac)2/H2O(31,Ca) | 0.30 | 0.10 | 0.99 | 70 |
| 19-11 | 9.65 | 10% Mg(Ac)2/H2O(14,Mg) | 0.20 | 0.04 | 0.55 | 64 |
| 19-17 | 8.99 | 10% Ca(Ac)2/H2O(28,Ca)a | 0.43 | 0.13 | 0.59 | 27 |
| 19-23 | 8.06 | 10% Mg(Ac)2/H2O(16,Mg) | 0.31 | 0.10 | 0.66 | 53 |
| 21-12 | 10.15 | 5% Ca(Ac)2/H2O(13,Ca) | 0.17 | 0.02 | 0.52 | 68 |
| 21-15 | 10.10 | 10% Mg(Ac)2/ | 0.41 | 0.03 | 0.53 | 22 |

TABLE I-continued

High Temperature Fouling Apparatus Results
1300–1500° F. Furnace Steam/Air Decoke;
1500–1880° F. Furnace Af/N2/Steam
1880° F. Furnace Propane (0.5 SCFM)/Steam/Af for 2.67 Hr.

| Run # | Steam Ml/Min | Antifoulant (ppm, Metal) | Coke Gms | Gray Gms | Pred (1) Coke Gms | % Coke (2) Reduction |
|---|---|---|---|---|---|---|
| 24–5 | 9.98 | 10% Mg(Ac)2/H2O(15,Mg) | 0.70 | 0.04 | 0.47 | −50 |
| 24–8 | 9.86 | 10% Ca(Ac)2/H2O(15,Mg) | 0.23 | 0.05 | 0.47 | 51 |
| 24–16 | 10.21 | 10% Mg(Ac)2/H2O(16,Mg) | 0.87 | 0.09 | 0.46 | −91 |
| 25–12 | 9.69 | 10% Mg(Ac)2/H2O(15,Mg) | 0.16 | 2.66 | 0.48 | 67 |
| 34–5 | 9.83 | 10% Ca(Ac)2/H2O(34,Ca) | 0.26 | 0.65 | 0.75 | 65 |
| 34–6 | 8.44 | 10% Mg(Ac)2/H2O(20,Mg) | 1.05 | 4.32 | 0.87 | −20 |
| 34–12 | 9.56 | 5.7% CaCl2/H2O(35,Ca) | 0.90 | 2.55 | 0.77 | −17 |
| 34–13 | 10.83 | 17.22% MgCl2/H2O(33,Mg) | 0.60 | 2.35 | 0.68 | 11 |
| 34–14 | 10.47 | 10% Ca(Ac)2/H2O(34,Ca) | 1.06 | 1.53 | 0.70 | −50 |
| 34–15 | 13.89 | 10% Mg(Ac)2/H2O(17,Mg)a | 0.91 | 2.02 | 0.53 | −71 |
| 35–2 | 8.63 | 10% Ca(Ac)2/H2O(36,Ca)a | 1.35 | 0.75 | 0.86 | −58 |
| 35–3 | 9.37 | 10% Mg(Ac)2/H2O(20,Mg)a | 0.45 | 0.82 | 0.79 | 43 |
| 35–4 | 8.54 | 5.7% CaCl2/H2O(37,Ca) | 0.40 | 0.84 | 0.86 | 54 |
| 35–5 | 9.95 | 17.22% MgCl2/H2O(34,Mg)a | 0.62 | 0.45 | 0.74 | 16 |
| 35–8 | 13.31 | 10% Mg(Ac)2/H2O(18,Mg) | 0.36 | 1.46 | 0.55 | 35 |
| 35–13 | 8.58 | 10% Ca(Ac)2/H2O(36,Ca) | 0.68 | 3.24 | 0.86 | 21 |
| 37–10 | 13.73 | 10% Ca(Ac)2/H2O(32,Ca) | 0.51 | 0.56 | 0.54 | 5 |
| 38B–4 | 9.64 | 30% MgSO4/H2O(49,Mg)a | 0.28 | 0.36 | 0.77 | 63 |
| 38B–5 | 9.25 | 30% Mg(NO3)2/H2O(49,Mg) | 0.19 | 0.28 | 0.80 | 76 |
| 38B–6 | 9.80 | 20% Ca(NO3)2/H2O(66,Ca) | 0.32 | 0.36 | 0.75 | 58 |
| 38B–17 | 10.92 | 20% Ca(NO3)2/H2O(65,Ca) | 0.23 | 0.29 | 0.68 | 66 |
| 38B–18 | 10.84 | 30% Mg(NO3)2/H2O(46,Mg) | 0.23 | 0.41 | 0.68 | 66 |
| 39–6 | 5.33 | 20% Ca(NO3)2/H2O(79,Ca) | 1.94 | 1.04 | 1.38 | −40 |
| 39–7 | 6.06 | 30% Mg(MO3)2/H2O(55,Mg) | 0.86 | 0.49 | 1.22 | 29 |
| 39–11 | 4.90 | 20% Ca(NO3)2/H2O(79,Ca) | 2.02 | 0.52 | 1.51 | −34 |
| 41–9 | 4.58 | 20% Ca(NO3)2/H2O(44,Ca) | 2.16 | 0.36 | 1.61 | −34 | a - Plugged Anitfoulant Injection Line
(1) - Predicted Coke = A/Condensate Rate ml/min where A = 5.32 for runs in furnace tubes 18 to 22, 4.65 for furnace tubes 24 to 30 and 7.38 for furnace tubes 34 to 41.
(2) - % Coke Reduction = [1-Coke/Pred Coke]*100

Average coke reductions obtained for each alkaline earth compound are summarized in Table II.

TABLE II

Summary of Effects on Coke Reduction of Various Alkaline Earth Compounds as Tested in The High Temperature Fouling Apparatus

| Compound | # of HFTA Runs | Metal (ppm) Range | Average Coke Red (%) | Mann-Whitney Confidence Limit |
|---|---|---|---|---|
| Ca(Ac)2 | 10 | 33–36 | 24 | 97.3 |
| CaCl2* | 2 | 35–37 | 19 | 78.0 |
| Ca(NO3)2 | 5 | 44–79 | 3 | 52.8 |
| All Calcium Treated | 17 | 33–79 | 17 | 95.5 |
| Mg(Ac)2 | 10 | 14–20 | 5 | 83.6 |
| MgCl2 | 2 | 33–34 | 14 | 65.0 |
| Mg(NO3)2 | 3 | 46–55 | 57 | 99.3 |
| MgSO4 | 1 | 49 | 63 | 95.6 |
| All Magnesium Treated | 16 | 14–55 | 20 | 98.7 |
| Blank | 62 | — | 0 | — |

*One run treated with CaCl2 was determined to be an "outlier" and was eliminated from the data listing due to its excessive coking and negative coking reduction of −314%.

The confidence limit that the pool of coke reductions for each set of treated runs were greater than the pool of coke reductions for the untreated control runs was determined using the well-known Mann-Whitney statistical procedure. As shown in Table II, the calcium acetate, magnesium nitrate or magnesium sulfate treated runs exhibited Mann-Whitney confidence limits in excess of 95%, a level generally accepted as significant. When the coke reduction levels for the 17 calcium treated HTFA runs were pooled and compared to the pooled coke reduction levels of the 62 untreated HTFA runs, a confidence limit of 95.5% was obtained. These 17 runs exhibited an average coke reduction level of 17%. Similarly, the pooled coke reduction levels for the 16 magnesium treated runs exhibited 20% average coke reduction and a confidence limit of 98.7%.

Accordingly, from the above, it is clear that the alkaline earth (Group IIa) metal salts such as the acetates, chlorides, and nitrates of calcium or magnesium and magnesium sulfate are effective as coke retarding treatments under the simulated pyrolysis conditions above noted. They therefore would be expected to perform well at commonly encountered pyrolytic temperatures such as from 1400° F.–2100° F. Desirably, the salts should be added to the pyrolytic steam and/or hydrocarbon feedstock in an amount that will provide about 0.1–5000 ppm of the desired Group IIa alkaline earth metal, such as calcium or magnesium metal, per million parts of the hydrocarbon feedstock. Based upon experimental data presently available, a preferred feed range is from about 5–100 ppm calcium or magnesium metal per million parts feedstock.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

I claim:

1. A method of inhibiting the formation and deposition of pyrolytic coke on the heated metal surfaces of the structural and associated parts of a pyrolysis furnace which is being used to crack a petroleum feedstock to produce lower and/or olefinic hydrocarbon fractions, which method comprises adding to the feedstock a coke inhibiting amount of a compound selected from the group consisting of calcium acetate, magnesium acetate, magnesium nitrate and calcium nitrate.

2. A method as recited in claim 1 wherein said compound comprises magnesium nitrate.

3. A method as recited in claim 1 wherein said compound comprises magnesium nitrate.

4. A method as recited in claim 1 wherein said compound comprises calcium nitrate.

5. A method as recited in claim 1 wherein said metal surfaces are heated, during said cracking, to a temperature of about 1400° F. or higher.

6. A method as recited in claim 1 wherein said compound is dissolved in a polar solvent.

7. A method as recited in claim 6 wherein said polar solvent is water.

8. A method as recited in claim 6 wherein said polar solvent is an alcohol.

9. A method as recited in claim 1 wherein the hydrocarbon is mixed with steam for enhancement of the cracking thereof.

10. A method as recited in claim 1 wherein said compound is added to said feedstock during cracking thereof.

11. A method as recited in claim 1 wherein said compound is added to said feedstock prior to cracking.

12. A method as recited in claim 1 wherein the compound is added to said feedstock in an amount so as to provide about 0.1–5,000 parts of said magnesium or calcium per million parts of feedstock.

13. A method as recited in claim 12 wherein said compound is added to said feedstock in an amount so as to provide about 10–100 ppm of said magnesium or calcium per million parts of feedstock.

14. A method as recited in claim 1 wherein the feedstock is ethane, propane, butane, light naphtha, heavy naphtha, gas oil or mixtures of same.

15. A method as recited in claim 1 wherein said feedstock is ethane, propane, or butane or mixtures thereof.

16. A method as recited in claim 1 wherein said compound comprises magnesium acetate.

* * * * *

UNITED STATES PATENT AND TRADEMARK OFFICE
CERTIFICATE OF CORRECTION

PATENT NO. : 4,889,614

DATED : December 26, 1989

INVENTOR(S) : Forester

It is certified that error appears in the above-identified patent and that said Letters Patent is hereby corrected as shown below:

Col. 5, line 29, "Test Procedure" should be centered.
Col. 5, line 30, delete "Test Procedure".

Col. 5, line 45, after temperature, please insert --- ( ---.

Claim 3
Col. 9, line 5, please delete "magnesium nitrate" and substitute therefor --- calcium acetate ---.

Signed and Sealed this

Sixteenth Day of April, 1991

Attest:

HARRY F. MANBECK, JR.

Attesting Officer

Commissioner of Patents and Trademarks